United States Patent [19]

Siu

[11] Patent Number: 5,302,836
[45] Date of Patent: Apr. 12, 1994

[54] HIGH SPEED IMAGE ACQUISITION FOR MICROELECTRONICS INSPECTION

[76] Inventor: Bernard Siu, 732 N. Diamond Bar Blvd., Diamond Bar, Calif. 91765

[21] Appl. No.: 914,541

[22] Filed: Jul. 16, 1992

[51] Int. Cl.$^5$ .......................................... G01N 21/88
[52] U.S. Cl. ................................... 250/572; 356/237
[58] Field of Search ........... 250/571, 572, 562, 227.20, 250/227.28; 356/237, 430

[56] References Cited

U.S. PATENT DOCUMENTS

| | | | |
|---|---|---|---|
| 4,284,353 | 8/1981 | Yoshida et al. | 250/227.28 |
| 4,688,939 | 8/1987 | Ray | 250/572 |
| 4,816,686 | 3/1989 | Hara et al. | 356/237 |
| 4,882,498 | 11/1989 | Cochran et al. | 250/571 |
| 5,032,735 | 7/1991 | Kobayashi et al. | 250/572 |
| 5,088,828 | 2/1992 | Doemens et al. | 250/227.28 |

Primary Examiner—David C. Nelms
Assistant Examiner—K. Shami
Attorney, Agent, or Firm—Leo R. Carroll

[57] ABSTRACT

This invention is a high speed illumination apparatus and technique which isolates bond wires, ball bonds, bond wedges and microcircuit chips exclusively for manual or high speed automatic inspection of microelectronics assemblies. This system consists of multiple concentric rings of illumination, which are focused towards the center of the rings, but from different angles of incident. Light from these angles reflect off the different specular surfaces of the bond wires, wire bonds, and bond wedges, providing background contrast. Light projected on the flat surfaces of microchip bodies tends to be absorbed, producing a negative contrast shadow if the other elements are illuminated in parallel. Unique angles of incidence provide substantial illumination contrasts between the areas of interest and its neighboring surfaces. The reflections provide unique signatures which are easily distinguishable by an image processing system. Alternating the transmission of light through each of the rings at high speed using electronic shutters, contrasted images with unique features can be highlighted exclusively in milliseconds. These contrasted images are then captured by a light responsive transducer such as a video camera for further fault determination.

22 Claims, 5 Drawing Sheets

HIGH SPEED IMAGE ACQUISITION FOR MICROELECTRONICS INSPECTION

BACKGROUND OF THE INVENTION

The U.S. Government has a paid up license in this invention and the right in limited circumstances to require the patent owner to license others on reasonable terms as provided for by the terms of contract No. DAAL02-89-C-0085, awarded by the Department of the Army.

1. TECHNICAL FIELD

This invention relates generally to methods and apparatus for high speed inspection of microelectronic device connections, and in particular to equipments used to illuminate interconnect wire bonds, ball bonds, and wedge bonds so as to improve discrimination against similar appearing backgrounds.

Typically, gold wires, gold bonds, and gold terminations are viewed against a gold background by manual inspection under a microscope. Since the field of view is normally less than one-eighth ($\frac{1}{8}$) of an inch, uniform illumination is needed to highlight the area of interest. The most common uniform illumination source is a circular ring light directing illumination perpendicularly or at a slight angle off normal onto the surface to be inspected. While this type of lighting works rather well under a microscope, the glares and shiny hot spots from the gold connections and the reflective backgrounds are often ignored by the operators, and they tend to interpolate, or "fill in" dark missing fragments of the images. Variations in such human judgments are a cause of inconsistent inspection results. For instance, the incremental fill in of a dark position on a wire may actually hide a break in the wire at that point.

With the recent development of machine vision technologies, attempts were made to inspect these gold interconnects and gold terminations per Mil-Std-883 Method 2017. Machine vision technologies, however, have not reached the sophistication of ignoring hot spots or filling in fragments in a random basis as a human being could. The approach, therefore is to develop an illumination technique, capable of isolating the specular interconnect wires, ball bonds, bond wedges and chips exclusively from its reflective backgrounds. In other words, provide a better contrast between the object of interest from its neighboring background. In addition, the illumination techniques must be fast enough to support machine vision technologies used for the image acquisition and processing of microelectronics inspection tasks.

2. BACKGROUND ART

Early improvements in inspection methods were concerned with better work-piece illumination, more accurate location, object image acquisition, flaw identification, recognition and finally rejection against given criterion. The focus of evolutionary inventive steps in these directions may be seen by overview of the following patents:

The need for diffused lighting to reduce reflections and shadows in close-up photography has been long recognized. Shank, in U.S. Pat. No. 3,737,226 discloses apparatus in which an indirect light source illuminates a small object through a series of pyramidal reflectors. Light is thus diffused around four sides of the object before reflection to a camera. This invention was for close-up photography and would have limited value for high speed inspection of microelectronic elements.

Kanade et al., in U.S. Pat. No. 4,427,880, provide an array of discrete light-emitting sources which are used to sequentially illuminate a symmetrical work piece object. Reflections are focused on a light responsive position sensor so as to provide continuous indications of distance, surface orientation and curvature of the object. Details of surface geometry are not provided. This approach is most effective for measuring distance if the reflective surface is flat. Based on the position of the reflected light spots on the surface, the distance between the surface and the optical sensor can be calculated and determined. The system does not use continuous illumination for visual identification of the object and its orientation. U.S. Pat. No. 4,508,452 to DiMatteo et al provides for determining the surface profile of an object by projecting a pre-coded pattern onto the surface. By matching the newly acquired image pattern to a pre-determined image pattern, the profile of the newly acquired image can be extracted. An object surface is scanned by a moving projector and subdivided into the large number of coded sections. Comparisons are made of progressive photographs of the work-piece with those of a standard reference surface. The entire surface of an object may therefore be mapped. The system is not applicable to improving contrast between very small three dimensional objects, such as wires, and the reflective background.

Imamura et al. in U.S. Pat. No. 4,568,835, detects foreign matter such as dust particles on a plane substrate by means of scattering of the reflections from a laser beam. As a specimen work-piece such as a photomask is scanned by an oblique incidence laser illumination beam, reflections from foreign materials are less directly scattered than are those from the edges of the circuit pattern. The illumination incidence angle is 80 to 60 degrees off normal, with a portion of the beam being reflected from the substrate surface while the remainder is refracted into the substrate medium from which it is internally reflected then externally scattered outward. This approach does not consider circular illumination used with a highly reflective, low refractive background medium.

In a different surface measurement application, Schachar, in U.S. Pat. No. 4,695,163, determines the contour of a cornea by scanning the surface with coherent light from different positions along a rectilinear path. Reflections received by detectors along the track are maximally polarized when the incidence angle equals Brewsters's angle. From a knowledge of the index of refraction of the medium and of Brewster's angle, the relative spacial locations of points over the surface may be determined. The system should provide slow but precise information when a refracting medium is under inspection, but will have limited utility with highly reflective objects.

An object locating system for use with robotic systems is described in U.S. Pat. No. 4,791,482 to Barry et al. The system projects a known geometrical image from a light source onto the surface of an object. The plane of the image on the object is determined by finding a normal to the surface from known geometrical relationships. Comparison of normals at different surface points are used to calculate distances and angles between the points. Gaussian images are generated for comparison between referenced objects and the unit under test.

In the field of solder joint inspection systems, Sanderson in U.S. Pat. No. 4,876,455 discloses a fiber optic solder joint inspection approach, in which light from multiple sources is reflected from a specular object to a fixed array of transducers. The individual light sources are derived from a single source which is scanned and piped to a plurality of optical fibers which lead to individual openings spaced around a semicircular illumination frame. For a given surface attitude, reflections to the fixed transducers will result from only one illumination source, assuming essentially specular reflection from the surface. Given known surface features of the object, an approximate reconstruction of the shape is made. The point source is usable with solder joint fillet inspection, but not with the variably curved and positioned wiring connections of microelectronic assemblies.

A related invention, U.S. Pat. No. 4,988,202 to Nayar et al, extends the above approach to include generation of an Extended Gaussian Image representation of a solder joint which is then evaluated as to acceptability.

A system for inspection of the uniformity of the surface of a flat circuit board component such as a dual inline package, employing computer vision is taught by Chemaly in U.S. Pat. No. 4,972,493. Illumination is provided by low angular light at the surface edge. Anomalies on the flat surface of dual in-line packages are inspected for pits, holes, blisters, grease, marks, chips and cracks Marks on the surface are distinguished from planned surface irregularities by comparison of grey scale brightness. The two directional lighting is not developed for specular surfaces such as wires, bonds and wedges.

Inspection of the circuit board components when soldered in place is taught by Ikegaya et al. in U.S. Pat. No. 5,027,418. Component lighting is provided by a standard ring illuminator positioned normal to the board. Board masking is provided to make an assessment of soldering condition independent of component lead placement on the circuit board lands.

It may be noted that none of the above inspection systems treat identification and inspection of variably curved and placed circuit elements such as microelectronic wires and bonds. Further, none teach the use or advantages of dual annular illumination sources, each disposed at different angular relationships with respect to normal, each of which provides optimal viewing contrasts for different classes of microelectronic wires and bonds relative their similar background.

DISCLOSURE OF INVENTION

The present invention is directed to improved systems for inspection of microelectronic assemblies, including the interconnect wires, ball bonds, and wedge bonds contained therein. Inspection of such devices today often uses a comparative method. Magnified projections of a reference sample and of the unit under inspection are visually compared on adjacent or split screens. The human inspector visually does the comparison and makes a subjective pass or fail judgement based upon their experience and training. The method is time consuming and produces inconsistent inspection results.

Replacement of the human operator with an automatic inspection machine involves overcoming three (3) major obstacles. The first obstacle is to be able to "see" and isolate objects of interest from their background. For instance, gold wires, gold wire bonds, and gold wedges must be identified against gold or similar backgrounds in a manner somewhat similar to that used by a human inspector to acquire the image. The second obstacle is to make pass or fail decisions based upon perceptions of the acquired image. The final obstacle is to repeatedly solve the first two problems at a rate beyond the capability of the human operator.

This invention comprises high speed illumination apparatus for highlighting the specular surfaces of interconnect bond wires, ball bonds, bond wedges and microcircuit chips commonly used in microelectronics assemblies.

Apparatus for implementing this invention includes multiple concentric rings of illumination from which light is directed toward the center of the rings. In operation, the area of interest on the microcircuit assembly is placed directly under the focused center of these concentric rings. The angle of incidence for each of these rings is unique, one for interconnect bond wires and ball bonds, while the other is for bond wedges. The combination of both rings is used for isolating microcircuit chips As light is transmitted via the first ring, an annular layer of illumination is transmitted and focused onto the microcircuit surface from a predetermined angle of incident. Light from this angle of incidence reflects off the specular surface of the bond wires and ball bonds, presenting unique reflective signatures to an array of light responsive transducers, such as video cameras which are arranged to view along the vertical axis through the concentric centers of the ring lights. Similarly, when a second ring is energized, unique reflective signatures on the bond wedges are created. Finally, energizing both of the rings simultaneously, the non-reflective surfaces of the microcircuit chips can be distinguished amongst its reflective neighboring surfaces.

It has been determined that optimal angles of incidence relative to the tangent of the reflective surface can be found for different classes of objects. Since the reflective surface of the bond wire is cylindrical, for instance, illumination from any angle should produce the same reflective result to the video camera. Limitations arise however, when one has to consider the gold conductor traces the bond wires have to bridge over. These conductor traces form a gold background which have approximately the same reflective angle as the gold wires, thereby causing the bond wires to "disappear" into its background. It is found in this invention that by lowering the angle of transmission to between 75 and 85 degrees from the vertical axis, light reflected from conductor trace surfaces is directed away from the video camera, while the light reflected from part of the cylindrical surface reflects directly to the video camera, providing a significant contrast between the bond wires over the conductive traces.

In the case of the wedge bonds, the physical feature is quite different than that of the cylindrical surface of the bond wire. Its features result from the stamping process in which the bond wire is pressed onto the gold surface by the capillary tube of a typical wire bonding machine. This stamping process flattens part of the cylindrical wire forming a flat reflective surface at the wedge site. This flattened reflective surface changes from the slope angle of the wire to that of the horizontal surface of the substrate. This sloped surface provides a mirror like reflective surface as well as a unique signature compared to that of a bond wire. It is expected that the optimal angle of light transmission will be different relative to the round wire. It has been found in this invention that, by shifting the light transmission angle to between 25 and 35 degrees from the vertical axis, optimal contrast between the wedge reflective surface and the conductive traces can be obtained.

Highlighting the microcircuit chip exclusively from the bond wires, wedges and balls is achieved by using the reflectivity differences between their surfaces. Microcircuit chips have a rough surface and are black in color, therefore, reflects a minimum amount of light. By transmitting full illumination through both ring lights, all areas around the chip are flooded with light while the microchip remains as a dark object. The outline of this microchip is acquired by the video camera for determination of the chip location, orientation, shape and size as necessary.

By alternating the light transmission through each of these rings at high speed, reflective signatures of interconnect wires, ball bonds, bond wedges and microcircuit chips can be captured by the light responsive transducers respectively and exclusively. Based on the known light speed and distances between our claimed transmission source and light responsive transducers, elapsed time between transmission to image capture is calculated to be 3 nanoseconds. Our claimed design permits the alternating of illumination sources in less than 4 milliseconds using electronic shutter means. The speed of highlighting microelectronics components is therefore limited by the performance speed of managing illumination transmission through each of the ring lights.

With the foregoing drawbacks of the prior art in mind, it is a prime object of the present invention to provide illumination methods and apparatus capable of improving the visual contrast between the interconnect wires, ball bonds, bond wedges and chips within a microelectronics assembly from their reflective backgrounds.

It is another object of the invention to provide such contrast improvement when the items to be discriminated are made of a reflective material similar to that of the background, such as gold.

Yet another object of this invention is to provide a first annular concentric ring of illumination which focuses light at a first angle of incidence on centered microelectronic interconnect bond wires or ball bonds, so that their vertically reflected images will be visually sensed with a maximum contrast relative to their similar background reflections.

Still another object of the invention is to provide a second annular concentric ring of illumination which focuses light at a second angle of incidence on centered microelectronic bond wedges, so that their vertically reflected images will be visually sensed with a maximum contrast relative to their similar background reflections.

A further object of the invention is to provide two annular concentric rings of illumination, each of which focus light in combination at unique angles of incidence on centered non-reflective microelectronic chips, so that their vertically reflected outline images will be visually sensed with a maximum contrast relative to their background reflections.

An additional objective is to provide a high speed illumination system which is fast enough to support automatic machine vision equipments used for non contact image acquisition and processing of microelectronics inspection data.

An additional objective is to provide a high speed illumination and non contact image acquisition system which is fast enough to support automatic machine vision equipments used for processing of microelectronics inspection data.

The above and other objects, features and advantages of the present invention will become more apparent from the following description when making reference to the detailed description and to the accompanying sheets of drawings in which preferred structural embodiments incorporating the principals of this invention are shown.

BRIEF DESCRIPTION OF THE DRAWINGS

The details of my invention will be in connection with the accompanying drawings, in which.

Best Mode for Carrying out the Invention Description of Microelectronics

Figure 1:
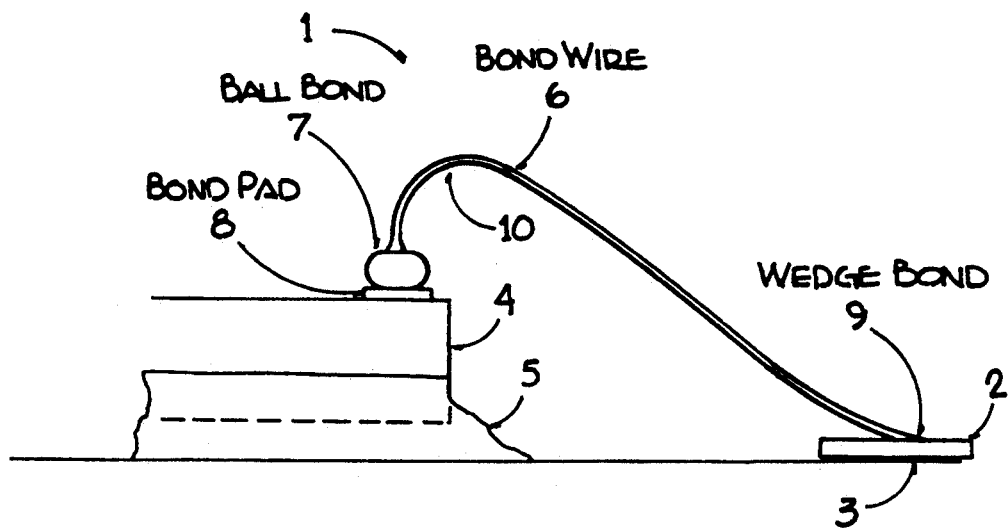
FIG. 1 is a partial side elevation view of a microelectronics assembly, showing a typical interconnection between a microcircuit chip and a conductor trace on a substrate.

Appreciation of the novelty of this invention starts with an understanding of common interconnection methods used in microelectronic assemblies. FIG. 1 is a partial side elevation view of such a microelectronics assembly, showing a typical interconnection between a microcircuit chip and a conductor trace on a substrate.

Figure 2:
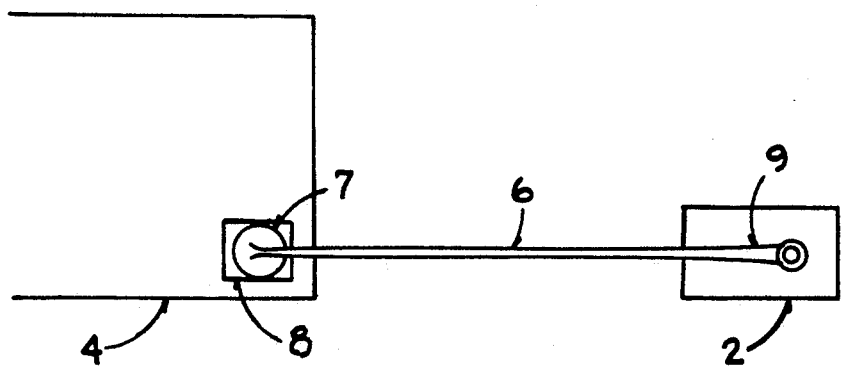
FIG. 2 is a partial top view of the typical interconnection depicted in FIG. 1.

FIG. 2 shows a partial top view of the same interconnection depicted in FIG. 1. Referring to FIGS. 1 & 2, microcircuit assembly 1 generally includes a typical conductive circuit pattern 2 printed on the surface of base substrate 3, usually made of a ceramic material. Microcircuit chip 4 is normally a cube-shaped integrated circuit which is attached onto substrate 4 using conductive or non-conductive epoxy 5. The electrical connection between the microchip circuit and the conductive traces on the substrate is made via cylindrical gold wire 6, typically 0.001 inch in diameter. The attachment of one end of the wire onto the microchip surface takes the shape of a flattened gold ball 7, subsequently named a ball bond. The bonding site for this attachment is called bond pad 8, and normally is a square conductive pad, situated along the edge of microchip 4. The opposite end of wire 6 is attached onto the surface of substrate conductive trace 2 by a stamping process, which results in the form of a flattened wedge 9, subsequently named a wedge bond. Since the surfaces of microchip 4 and the conductive pad 2 are at different heights, the bond wire 6 takes the form of a wire loop 10 between the two connections. This loop assures that bond wire 6 is prevented from touching the edge of the microchip 4, as well as providing adequate stress relief for the bond wire in the event of severe thermal stress and vibrations. Though ball bonds 7, bond wires 6, and bond wedges 9 are unique in their physical shape, they all possess highly specular surfaces. This invention, takes advantage of their specular surfaces and unique reflective signatures, and has provided apparatus and methods for presenting these images to light responsive transducers at high speed.

Illumination Concepts

Applying known physics principles of reflectivity, we know that for a reflective surface, the angle of reflection is equal to the angle of in incidence, measured from the axis perpendicular to the tangent of the surface. Under usual inspection circumstances, illumination is directed onto the microelectronics surfaces perpendicularly. The light striking the bond wires, ball bonds, and bond wedges scatters in all directions due to their specular and cylindrical surfaces. The gold conductor traces lying in the background also produce scattered light rays, the majority of which are directed vertically back toward the light source because the conductor trace surfaces are relatively flat. These reflected light are the main causes of misinterpretation of images by imaging machines as well as human operators. A key to this invention is the determination of the optimal angles of incidence for the bond wires, ball bonds and wedge bonds, such that maximum contrast between the objects and their neighboring background can be achieved.

Figure 3:
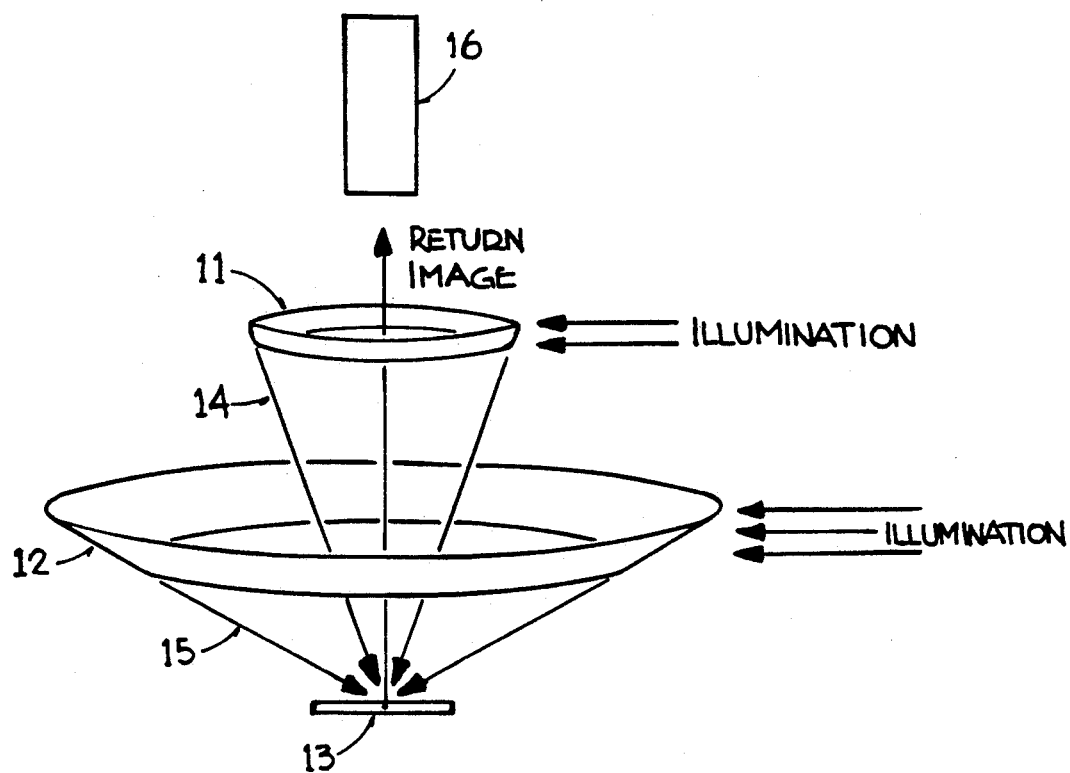
FIG. 3 is an isometric view of a pair of fiber optic bundles, disposed concentrically about the vertical axis between the work piece and the sensing camera.

As indicated in FIG. 3, this invention includes two light sources 11 and 12 affixed at the desired angles from the objects of interest 13 such that light rays 14 and 15 striking these objects of interest are reflected to the solid state camera 16 mounted along the vertical axis to the microcircuit. By feeding light into these sources sequentially or simultaneously, different objects can be highlighted respectively. For example, to highlight the bond wires and ball bonds, light 15 at 75 to 85 degrees is illuminated. On the other hand, if illumination of the wedge bonds is warranted, the light source 14 at 25 to 35 degrees is illuminated. Similarly, if the chips need to be highlighted, both the lights are illuminated.

Ring Illumination

Figure 4:
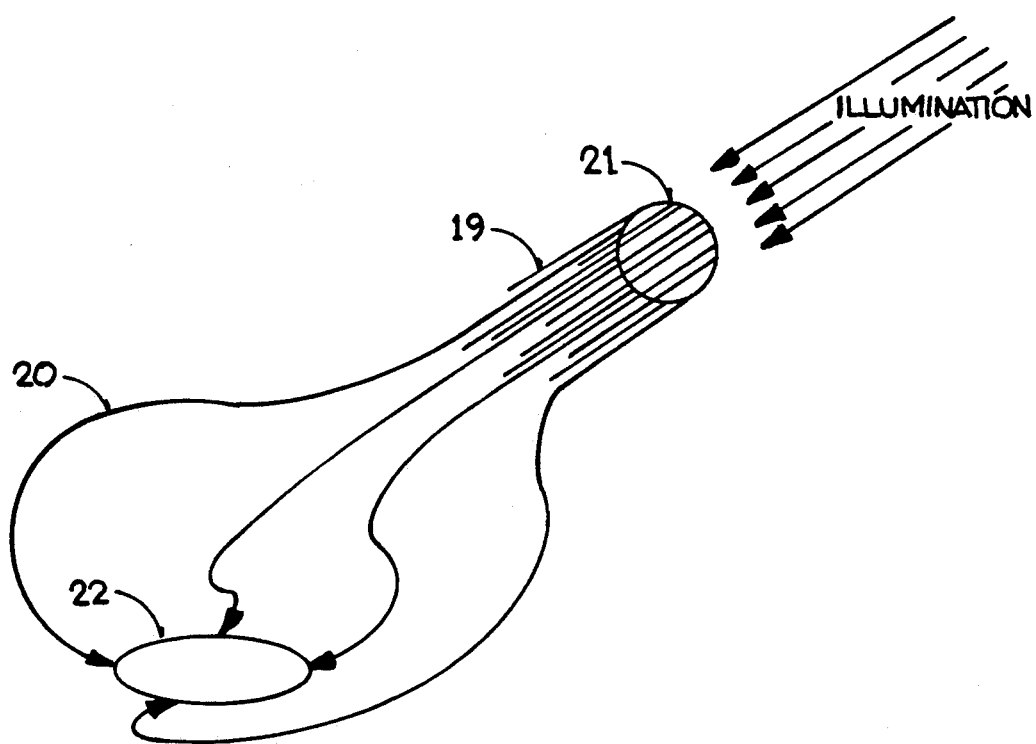
FIG. 4 depicts an illustrative plan layout of the arrangement of the fibers within each fiber optic bundle.

In the field of microelectronics, bond wires, ball bond, wedges and chips may be assembled in random directions. The illumination technique developed above, takes the form of multiple ring light configurations, while maintaining the angle of incidence. The lower angled ring light is for illuminating bond wires and ball bonds, the higher angled ring is for illuminating the wedges. Both rings are illuminated for maximum contrast for the microcircuit chips. As shown in FIG. 4, a fiber optics hardware version is used to describe the concept. This apparatus consists of two concentric ring lights made of optical fibers 20. Each fiber optics bundle for the rings are independent of each other. One end of the fiber is bundled in cylindrical shape 21 while the other end is fanned out into a circular configuration 22 with its ends pointing towards the center of the ring. As light is transmitted into the cylindrical end 21 of the fiber bundle 19, it travels coaxially along the length of the fiber optics bundle, and exits in a circular configuration 22 at a predetermined angle onto the surface of the microcircuit. The angle of incident is determined by the base of a housing on which the fiber optics bundle are attached. As light is sent through each of the bundles, different signatures of the microcircuit are highlighted.

Figure 5:
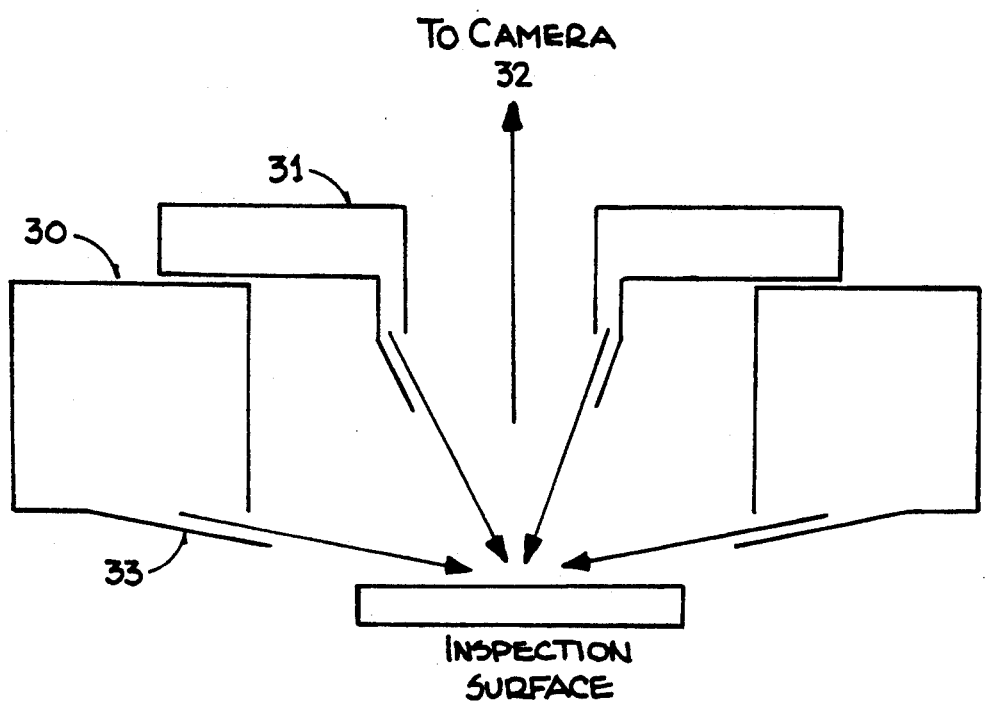
FIG. 5 presents a cross section view of the supporting housings for the fiber optic bundles.

In FIG. 5, a cross section is shown of the circular mechanical housing 30 with its base 33 machined to 80+ or −5 degrees from the vertical axis 32, which provides an angled platform on which the fiber optics threads 20 are bonded on. A second mechanical housing 31, similar to the first, except that it has a smaller diameter, with its base machined to 30+ or −5 degrees from the vertical axis provides support for its fiber optics bundle. The larger ring light is for illuminating the bond wires and the ball bonds, while the smaller ring is for illuminating wedges.

Using the above angles of illumination and the claimed apparatus, highlighted bond wires have an image signature of a highlighted wire, ball bonds take the shape of a highlighted ball, bond wedges take a lighted shape similar to a triangle and a microchip takes the shape of a black block among white surroundings when projected onto a video monitor via a video camera. By using the threshold function of a machine vision system, the entire wire span can be further isolated from its background.

High Speed Illumination

Figure 6:
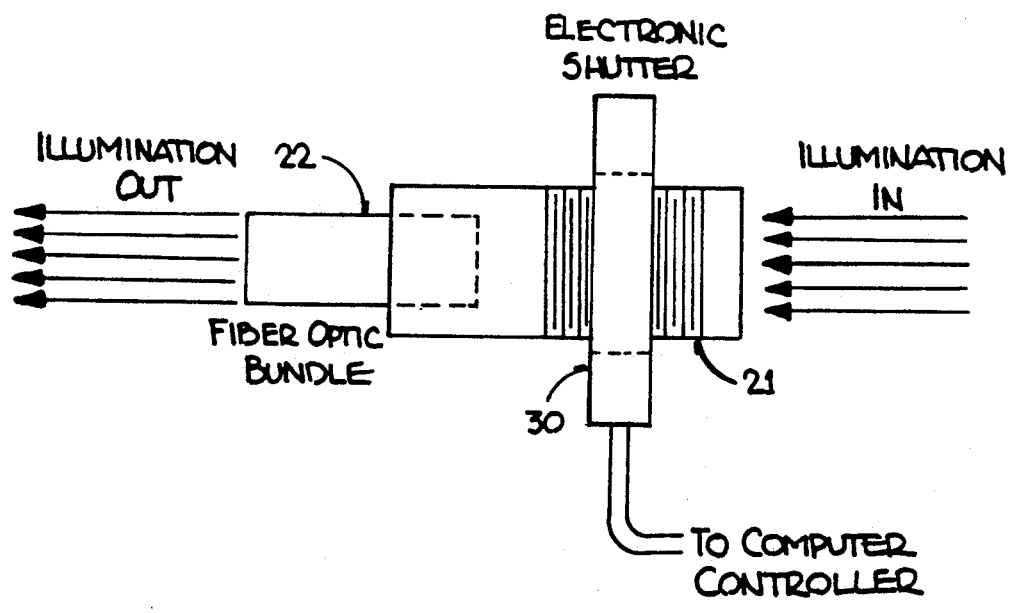
FIG. 6 shows a side view of an electronic shutter used at the interface between the light source and the fiber optic bundle.

To couple this invention to a machine vision system, a method for controlling these illumination optics alternately and simultaneously was developed. Since the standard image capture time by a video camera is 33 milliseconds, it is necessary to provide the planned illumination compatible to the said speed. A simple turning on and off, of the light source is not satisfactory for this application. This is because it requires a relatively long time duration for the light source to reach its full illumination rom null illumination. Conversely, it also requires an unacceptable time duration for the illumination to drain from full illumination to null illumination. In addition, residual illumination has a negative affect on the signatures for the following image. To overcome this obstacle, a constant "on" illumination is used to provide light to the cylindrical end of both bundles. However, in between the fiber optics bundle ends 21 and 22 and the light source, a high speed electronic shutter 30 is fitted in place as shown in FIG. 6. One electronic shutter is used for each bundle. Electronic shutters such as a Uniblitz Model LCS4 may be used. These shutters have the full opening time of 2.5 milliseconds and a full closing time of 1.3 milliseconds. The minimum dwell time or opening time is 0.9 milliseconds. In our application, the dwell time will be held at 35 milliseconds to accommodate the image capture time. The use of the shutters eliminate the glowing time for the light source before it reaches its full illumination and the residue illumination as the light source is being turned off.

With the above mentioned apparatus, the technique of providing high speed illumination for microelectronics assemblies such as bond wires, ball bonds, bond wedges and microcircuit chips comprise the following steps:

(a) The system controller commands the opening of one of the two electronics shutters (2.5 msec.), depending on the shutter chosen, light transmits through the fiber optics bundle and strikes the specular surfaces of the bond wires, ball bonds, or bond wedges on the microcircuit, sending a unique reflective signature to the video camera such as a Javelin Model JE7362 or equivalent.

(b) The video camera then captures an image for processing (33 msec.) while the shutter is being held open for 35 msec.

(c) Once the image is captured, the system controller issues a command and closes the shutter (1.3 msec.).

(d) This process repeats throughout the inspection cycle until all locations of the microelectronics assembly are inspected.

By opening and closing these shutters alternately or simultaneously, the microcircuit bond wires, ball bonds, wedges and dies can be acquired in 38.8 msec. It is important to note that the time for providing the intended illumination to the microcircuit is only (2.5+1.3) or 3.8 msec. The majority of the time is on image capture which is dependent on the image capture technology. As the speed of image capture technology improves, so will the speed of microelectronics inspection systems.

It should be noted that the system is not limited to inspection of microcircuits only. The high speed illumination technique can be used to control any predetermined illumination for automated inspection systems. By modifying the angle of incident of the illumination, inspection of many other small items having specular surfaces, such as solder joints, component leads, or machine parts can be supported by this invention.

The basic concepts of the techniques and apparatus for providing high speed illumination and the unique signatures of on microelectronics assemblies elements have been illustrated herein. Although the present invention has been described in considerable detail with reference to certain preferred embodiments thereof, other versions are possible. Therefore, the spirit and scope of the appended claims should not necessarily be limited to the description of preferred versions contained herein.

What is claimed is:

1. Illumination apparatus for inspection of microelectronic assemblies with internal microcircuit chips electrically connected by bonding to circuit conductive traces on a mounting substrate, wherein interconnect wires, ball bonds, bond wedges and chip bodies may be visually discriminated against similar reflective backgrounds, comprising:
   a plurality of circular ring light source means for illumination of said chips and interconnect wire bonding means placed at the focused annular ring center;
   means for focusing each said ring light source at a predetermined angle of incidence for optimal contrast between said chip bodies and interconnect means and similar reflective trace backgrounds; and
   an array of light responsive transducers arranged for image acquisition of reflections along a vertical axis through the concentric centers of both said ring lights.

2. Illumination apparatus according to claim 1, wherein each said circular ring light source is comprised of:
   a common source of focused light;
   a fiber optics cylindrical bundle of light conductors, having a first output end fanned out into a circular configuration for vertical projection onto the work object, and a second input end adjacent said light source; and
   angled housing means for supporting each said ring bundle at the angle required for each said prerequired angle of incidence.

3. Illumination apparatus according to claim 1, further comprising light switching means for sequential illumination from each said ring light source.

4. Illumination apparatus according to claim 3, further comprising light switching means for parallel illumination from selected combinations of said ring light sources.

5. Illumination apparatus according to claim 4, wherein said light switching means includes electronic stuttering means whereby switching rates are compatible with automatic machine vision equipments.

6. Illumination apparatus according to claim 4, wherein said plurality of circular ring light source means includes a first said ring light means directed at an illumination angle off vertical which is sufficiently large so as to separate the reflection from rounded inspection objects from conductor background traces made of a similar material.

7. Illumination apparatus according to claim 6, wherein said rounded objects include bond wires and ball bonds.

8. Illumination apparatus according to claim 7, wherein said rounded objects and the conductor background traces are made of gold.

9. Illumination apparatus according to claim 7, wherein said illumination angle is between 75 and 85 degrees off vertical.

10. Illumination apparatus according to claim 6, wherein said plurality of circular ring light source means further comprises a second said ring light means directed at an illumination angle off vertical which is sufficiently small so as to separate the reflection from inspection objects having variable sloped surfaces from substrate background traces made of a similar material.

11. Illumination apparatus according to claim 10, wherein said variable sloped objects include wedge bonds.

12. Illumination apparatus according to claim 11, wherein said variable sloped objects and the background traces are made of gold.

13. Illumination apparatus according to claim 11, wherein said illumination angle is between 25 and 35 degrees off vertical.

14. Illumination apparatus according to claim 10, wherein said first and second ring light means are simultaneously switched on so as to separate the reflection from inspection objects having flat body surfaces from other substrate and inspection object background reflections.

15. Illumination apparatus according to claim 14, wherein said flat sloped objects include reflective chip bodies.

16. Illumination apparatus according to claim 15, wherein said flat sloped objects include absorptive chip bodies.

17. Illumination apparatus for inspection of microelectronic assemblies with internal microcircuit chips electrically connected by bonding to circuit conductive traces on a mounting substrate, wherein absorptive chip bodies may be visually discriminated against similar reflective backgrounds, comprising:
   a plurality of circular ring light source means for illumination of said chips and nearby interconnecting wire bonding means placed at the focused annular ring center;

means for focusing each said ring light source at multiple angles of incidence for producing negative contrast between said absorptive chip bodies and other floodlit reflective backgrounds; and an array of light responsive transducers arranged for image acquisition of absence of reflections along a vertical axis through the concentric centers of both said ring lights.

18. Illumination apparatus according to claim 15, further comprising light switching means for parallel illumination from a plurality of combinations of said ring light sources for background illumination.

19. A method of providing illumination for inspection of microelectronic assemblies with internal microcircuit chips electrically connected by bonding to circuit conductive traces on a mounting substrate, wherein interconnect wires, ball bonds, bond wedges and chip bodies may be visually discriminated against similar reflective backgrounds, comprising the steps of:

providing a plurality of circular ring light source means for illumination of said chips and nearby interconnecting wire bonding means placed at the focused annular ring center;

supporting each said circular ring light source means in accordance with a predetermined angle so as project light at a predetermined incidence angle onto the area of interest being inspected;

switching between projected ring illuminations sequentially so as to optimize the contrast of rounded and tapered objects against background reflections; and detecting the unique reflective signatures by means of light sensitive transducers.

20. A method of providing illumination for inspection of microelectronic assemblies with internal microcircuit chips electrically connected by bonding to circuit conductive traces on a mounting substrate, wherein interconnect wires, ball bonds, bond wedges and chip bodies may be visually discriminated against similar reflective backgrounds according to the method of claim 19, wherein the step of providing a plurality of circular ring light source means for illumination of said chips and nearby interconnecting wire bonding means placed at the focused annular ring center is further comprised of:

providing a light source;

conducting the light source through multiple fiber optic strands arranged in bundles; and fanning the outputs from the multiple fibers of each bundle into a circular light ring arrangement for illumination of said chips and nearby interconnecting wire bonding means placed at the focused annular ring center;.

21. A method of providing illumination for inspection of microelectronic assemblies with internal microcircuit chips electrically connected by bonding to circuit conductive traces on a mounting substrate, wherein absorptive chip bodies may be visually discriminated against similar reflective backgrounds, comprising:

providing a plurality of circular ring light source means for illumination of said chips and nearby interconnecting wire bonding means placed at the focused annular ring center;

focusing each said ring light source at a plurality of angles of incidence for producing negative contrast between said absorptive chip bodies and other floodlit reflective backgrounds;

switching between projected ring illuminations simultaneously so as to increase the total background reflections; and detecting with an array of light responsive transducers arranged for image acquisition of absence of reflections along a vertical axis through the concentric centers of said light rings.

22. A method of providing illumination for inspection of microelectronic assemblies with internal microcircuit chips electrically connected by bonding to circuit conductive traces on a mounting substrate, wherein absorptive chip bodies may be visually discriminated against similar reflective backgrounds, according to the method of claim 21, wherein the step of providing a plurality of circular ring light source means for illumination of said chips and nearby interconnecting wire bonding means placed at the focused annular ring center is further comprised of:

providing a light source;

conducting the light source through multiple fiber optic strands arranged in bundles; and fanning the outputs from the multiple fibers of each bundle into a circular light ring arrangement for illumination of said chips and nearby interconnecting wire bonding means placed at the focused annular ring center.

* * * * *